US012797029B2

(12) United States Patent
Gao et al.

(10) Patent No.: US 12,797,029 B2
(45) Date of Patent: Nov. 17, 2026

(54) VETERINARY DR DEVICE AND CAPTURING GUIDANCE METHOD THEREFOR

(71) Applicant: Shenzhen Mindray Animal Medical Technology Co., Ltd., Shenzhen (CN)

(72) Inventors: Weiliang Gao, Shenzhen (CN); Ming Li, Shenzhen (CN); Liguo Zhang, Shenzhen (CN); Shengxi Wang, Shenzhen (CN)

(73) Assignee: Shenzhen Mindray Animal Medical Technology Co., Ltd., Shenzhen (CN)

( * ) Notice: Subject to any disclaimer, the term of this patent is extended or adjusted under 35 U.S.C. 154(b) by 310 days.

(21) Appl. No.: 18/501,687

(22) Filed: Nov. 3, 2023

(65) Prior Publication Data

US 2024/0197282 A1 Jun. 20, 2024

(30) Foreign Application Priority Data

Dec. 16, 2022 (CN) ......................... 202211627064.5

(51) Int. Cl.
*A61B 6/00* (2024.01)
*G06T 7/00* (2017.01)

(52) U.S. Cl.
CPC .............. *A61B 6/541* (2013.01); *A61B 6/542* (2013.01); *G06T 7/0012* (2013.01); *G06T 2207/10116* (2013.01)

(58) Field of Classification Search
CPC .......... A61B 6/541; A61B 6/542; A61B 6/508
See application file for complete search history.

(56) References Cited

U.S. PATENT DOCUMENTS

| | | | | |
|---|---|---|---|---|
| 9,665,254 B2 * | 5/2017 | Hayashi | G06F 3/04817 |
| 11,553,877 B2 * | 1/2023 | Kaneko | A61B 5/4504 |
| 11,769,588 B2 * | 9/2023 | Fukazu | G16H 30/40 378/98.5 |
| 11,918,401 B2 * | 3/2024 | Bailey, Sr. | A61B 6/508 |
| 2016/0081642 A1 * | 3/2016 | Okusu | A61B 6/4452 715/709 |
| 2016/0081650 A1 | 3/2016 | Okusu et al. | |
| 2022/0208365 A1 | 6/2022 | Vojan et al. | |
| 2024/0197282 A1 * | 6/2024 | Gao | A61B 6/04 |

FOREIGN PATENT DOCUMENTS

JP 201464776 A 4/2014

OTHER PUBLICATIONS

European Patent Office, Search Report in European Patent Application No. 23210779.7 (Mar. 15, 2024).

* cited by examiner

*Primary Examiner* — David J Makiya
(74) *Attorney, Agent, or Firm* — Leydig, Voit & Mayer, Ltd.

(57) ABSTRACT

Provided are a veterinary DR device and a capturing guidance method therefor. The method includes: obtaining at least two body positions for an animal to be tested; determining a current body position therefrom; displaying guidance information for the current body position; obtaining a medical image for the current body position after receiving an exposure start instruction input by the user; using, after detecting an exposure completion instruction triggered after obtaining the medical image for the current body position, a next body position to be tested according to a specified order; and displaying guidance information for the next body position.

14 Claims, 8 Drawing Sheets

300

300

Body position points: both forelimbs are pulled straight forward to expose the chest; both hind limbs are naturally extended and fixed, such that a midsagittal plane of the body is perpendicular to a bed board.

VETERINARY DR DEVICE AND CAPTURING GUIDANCE METHOD THEREFOR

CROSS-REFERENCE TO RELATED APPLICATIONS

This patent application claims the benefit of Chinese Patent Application No. 202211627064.5, filed Dec. 16, 2022, which is hereby incorporated by reference in its entirety.

TECHNICAL FIELD

The disclosure relates to the field of veterinary medical device technologies, and more specifically to a veterinary DR device and a capturing guidance method therefor.

BACKGROUND

In animal hospitals, veterinarians lack systematic professional training compared with human doctors. For example, when operating a veterinary DR device (that is, a digital X-ray photography system), medical care personnel often lack their own ability to determine whether positioning of animals is correct when radiographing. In addition, certain difficulties will also be encountered when radiographing animals, compared to radiographing humans. Animals cannot obey commands like humans, so even if medical care personnel know how to position animals, they cannot convey it to the animals, and it is therefore necessary for the medical care personnel to manually control postures or positions of the animals. When it is necessary to continuously capture images of the animals in a plurality of body positions, the medical care personnel have even more complicated work. The medical care personnel not only need to control the animals, but also need to operate the veterinary DR device. In this process, it may be necessary to find corresponding information to assist in determining whether the positioning for medical images is correct, which greatly affects the efficiency and concentration of the medical care personnel.

SUMMARY

According to a first aspect, an embodiment of the disclosure provides a veterinary DR device, including:

- a display;
- an X-ray emission module configured to generate an X-ray to penetrate an animal to be tested;
- an X-ray receiving module configured to receive the X-ray generated by the X-ray emission module, to convert the received X-ray into an electric signal;
- an imaging module configured to obtain a medical image based on the electric signal converted by the X-ray receiving module;
- a memory configured to store a plurality of pieces of guidance information, wherein each piece of guidance information is used for assisting a user to capture a medical image of the animal to be tested in a body position to be tested; and
- a processor configured to obtain at least two body positions to be tested that are selected by the user for the animal to be tested, determine a current body position from the at least two body positions to be tested, and control the display to display guidance information for the current body position;

- after receiving an exposure start instruction input by the user, control the X-ray emission module to emit the X-ray to the animal to be tested, for the purpose of obtaining a medical image for the current body position, and control the imaging module to obtain the medical image for the current body position based on the electric signal converted by the X-ray receiving module; and
- use, after detecting an exposure completion instruction triggered based on completion of obtaining the medical image for the current body position, a next body position to be tested as a new current body position according to a specified order, and control the display to display guidance information for the new current body position.

According to a second aspect, an embodiment provides a capturing guidance method for a veterinary DR device, including:

- obtaining at least two body positions to be tested that are selected by a user for an animal to be tested, wherein each of the body positions to be tested has a piece of preset guidance information, and each piece of guidance information is used for assisting the user to capture a medical image for a body position to be tested;
- determining a current body position from the at least two body positions to be tested;
- displaying guidance information for the current body position;
- obtaining a medical image for the current body position after receiving an exposure start instruction input by the user;
- using, after detecting an exposure completion instruction triggered based on completion of obtaining the medical image for the current body position, a next body position to be tested as a new current body position according to a specified order; and
- displaying guidance information for the new current body position.

According to the veterinary DR device and the capturing guidance method therefor in the above embodiments, after the current body position is determined, the display may display the guidance information for the current body position to assist the user in capturing the medical image for the current body position, which saves the time for the user to find information and improves user experience.

After the medical image is obtained, the veterinary DR device can automatically display, without other operations of the user, the guidance information for the next body position to be tested. As a result, the user may focus on posture adjustment of the animal and does not need to operate back and forth on an animal side and a veterinary DR device side. This ensures the continuity and efficiency of operations when obtaining medical images for a plurality of body positions to be tested.

DESCRIPTION OF THE PREFERRED EMBODIMENTS

Figure 1:
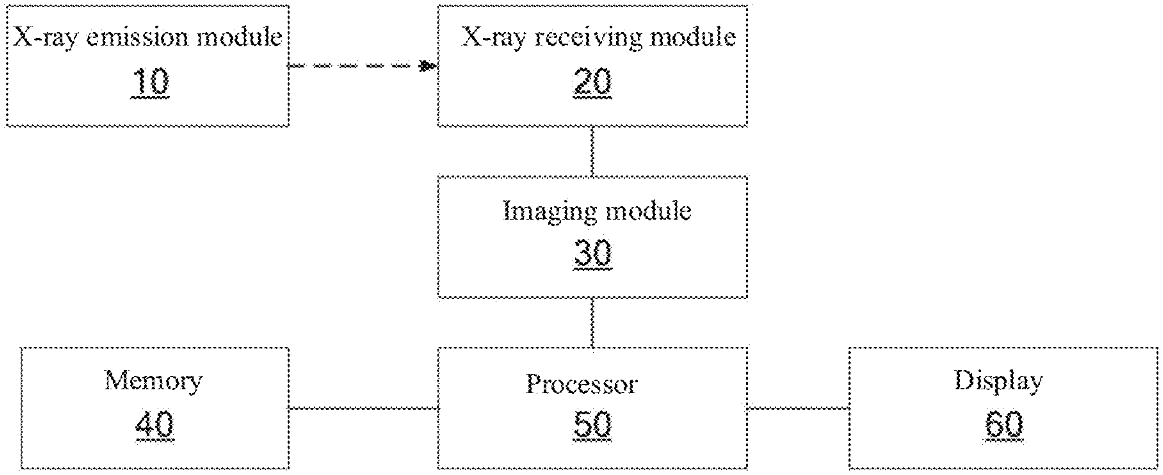
FIG. 1 is a schematic diagram of a hardware structure of a veterinary DR device, according to an embodiment.

The disclosure will be further described in detail below through specific implementations in conjunction with the accompanying drawings. Associated similar element reference numerals are used for similar elements in different implementations. In the following implementations, many details are described such that the disclosure may be better understood. However, it may be effortlessly appreciated by persons skilled in the art that some of the features may be omitted, or may be substituted by other elements, materials, and methods in different cases. In certain cases, some operations involved in the disclosure are not displayed or described in the specification, which is to prevent a core part of the disclosure from being obscured by too much description. Moreover, for persons skilled in the art, the detailed description of the involved operations is not necessary, and the involved operations can be thoroughly understood according to the description in the specification and general technical knowledge in the art.

In addition, the characteristics, operations, or features described in the specification may be combined in any appropriate manner to form various implementations. In addition, the steps or actions in the method description may also be exchanged or adjusted in order in a way that is obvious to persons skilled in the art. Therefore, the various orders in the specification and the accompanying drawings are merely for the purpose of clear description of a certain embodiment and are not meant to be a necessary order, unless it is otherwise stated that a certain order must be followed.

The serial numbers themselves for the components herein, for example, "first" and "second" are merely used to distinguish the described objects, and do not have any sequential or technical meaning. Moreover, as used in the disclosure, "connection" or "coupling," unless otherwise stated, includes both direct and indirect connections (couplings).

Existing veterinary DR devices usually have no special design for obtaining medical images for a plurality of body positions to be tested. However, in daily work, the inventor found that there are more cases in which human intervention is needed for positioning animals. If users may be free from the operation of the veterinary DR device, the work efficiency may be greatly improved. In view of this, a veterinary DR device of the disclosure can provide guidance information for a current body position, so as to avoid finding off-line information. In addition, the device automatically displays guidance information for a next body position to be tested, which especially has unique significance in the field of animal medical treatment.

Figure 2:
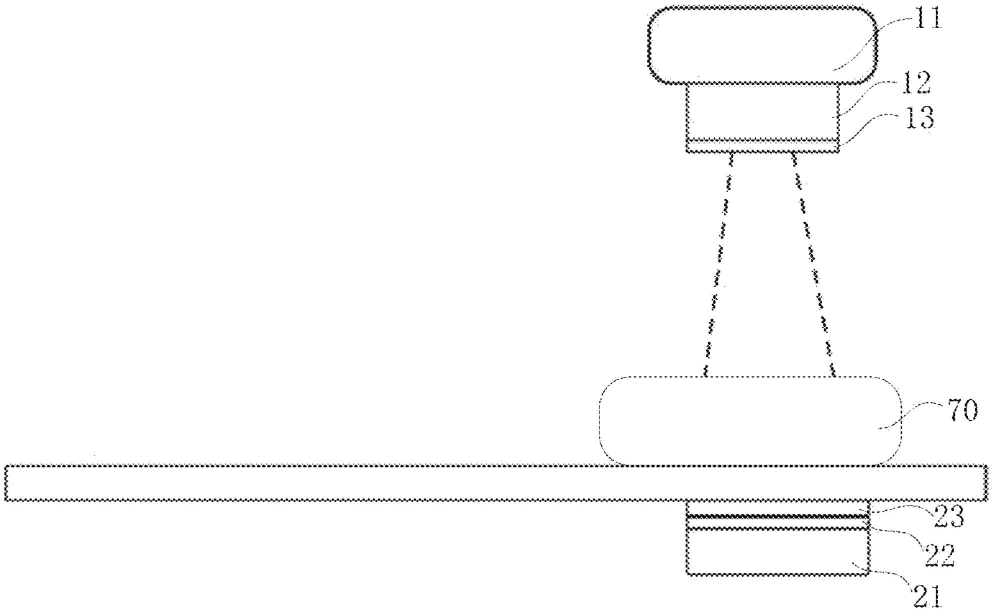
FIG. 2 is a schematic diagram of a structure of a veterinary DR device, according to an embodiment.

Referring to FIG. 1 to FIG. 2, an embodiment of the disclosure discloses a veterinary DR device. The veterinary DR device at least includes an X-ray emission module 10, an X-ray receiving module 20, an imaging module 30, a memory 40, a processor 50, and a display 60. It should be noted that, according to a capturing position of the machine, the veterinary DR device may be a standing-position photography system, a recumbent-position photography system, a free-position photography system, or a multi-position integrated photography system, and this is not limited in this embodiment of the disclosure. According to an operating mode of the machine positioning, the veterinary DR device may be manually adjustable or automatically adjustable, where for the manually adjustable veterinary DR device, a height/angle of the X-ray emission module 10, a height/angle of the X-ray receiving module 20, a capturing distance, and the like may be manually adjusted. For the automatically adjustable veterinary DR device, the height/angle of the X-ray emission module 10, the height/angle of the X-ray receiving module 20, the capturing distance, and the like may be adjusted through motor driving.

The X-ray emission module 10 is configured to generate an X-ray to penetrate an animal 70 to be tested. For example, the X-ray emission module 10 may include an X-ray tube filament as a cathode and target metal (such as tungsten and molybdenum) as an anode. Free electrons are generated near the cathode by supplying power to and heating the X-ray tube filament. When high voltage (tens or hundreds of kV) is supplied to the cathode and the anode, a potential difference between the cathode and the anode increases sharply. The electrons travel from the cathode to the anode at a high speed, bombarding the target metal of the anode to generate energy conversion, where less than 1% of energy is converted into X-rays, and more than 99% of energy is converted into heat energy, thus generating the X-rays.

In some embodiments, referring to FIG. 2, the X-ray emission module 10 includes a ray source 11, a beam limiter 12, and a filter 13. The beam limiter 12 and the filter 13 are sequentially arranged behind the ray source 11, the ray source 11 is configured to generate an X-ray, the beam limiter 12 is configured to shield unnecessary primary X-rays, and the filter 13 is configured to filter X-rays.

In some embodiments, a position (such a height, a horizontal position, or the like) and angle of the X-ray emission module 10 may be adjusted. The X-ray receiving module 20 is configured to receive the X-ray generated by the X-ray emission module 10, to convert the received X-ray into an electric signal.

For example, the X-ray receiving module 20 includes a front case, a ray conversion layer, a photoelectric conversion layer, a supporting structure, a circuit board, and a rear case. The ray conversion layer is configured to convert the ray into visible light. The ray conversion layer generally includes a scintillation layer or a fluorescent layer, which is configured to convert the ray into the visible light.

The scintillation layer is used as an example, and may generally be made of scintillation materials, typically such as cesium iodide (CIS), gadolinium oxysulfide (GOS), or the like. The photoelectric conversion layer may be a TFT matrix layer, and is configured to sense the visible light converted by the ray conversion layer and convert the visible light into the electric signal for image information collection.

In some embodiments, the X-ray receiving module 20 may be a flat panel detector 21 or an X-ray receiving module 20 in another form, and this is not limited in this embodiment of the disclosure.

In some embodiments, referring to FIG. 2, the X-ray receiving module 20 includes the flat panel detector 21, an ionization chamber 22, and a grid 23.

The ionization chamber 22 and the grid 23 are arranged in front of the flat panel detector 21 (between the animal 70 to be tested and the flat panel detector 21) and behind a bed board supporting the animal 70 to be tested, where the grid 23 is configured to eliminate scattered light and make the imaging of the imaging module 30 clearer, and the ionization chamber 22 is configured to measure ionization radiation.

The imaging module 30 is configured to generate, based on the electric signal converted by the X-ray receiving module 20, a medical image for a body position to be tested.

The memory 40 is configured to store a plurality of pieces of guidance information, where each piece of guidance information is used for assisting a user to capture a medical image of the animal to be tested 70 in a body position to be tested.

Forms of the guidance information include but are not limited to text, pictures, and videos. Content of the guidance information includes but is not limited to a positioning mode of the animal 70 to be tested, an operation key point of the veterinary DR device, etc., to guide the user to obtain a better medical image.

The processor 50 may be a nerve center and command center of the veterinary DR device, or a command center responsible for machine attitude control or display control in the veterinary DR device. The processor 50 may generate an operation control signal according to an instruction operation code and a timing signal to complete the control of instruction fetching and execution. In this embodiment, the processor 50 is configured to obtain at least two body positions to be tested that are selected by the user for the animal 70 to be tested, determine a current body position from the at least two body positions to be tested, and control the display 60 to display guidance information for the current body position.

In some embodiments, when the user selects the at least two body positions to be tested, corresponding priorities are assigned to the body positions to be tested.

For example, when the user selects the at least two body positions to be tested, a body position to be tested that is first selected has a higher priority.

Figure 3:
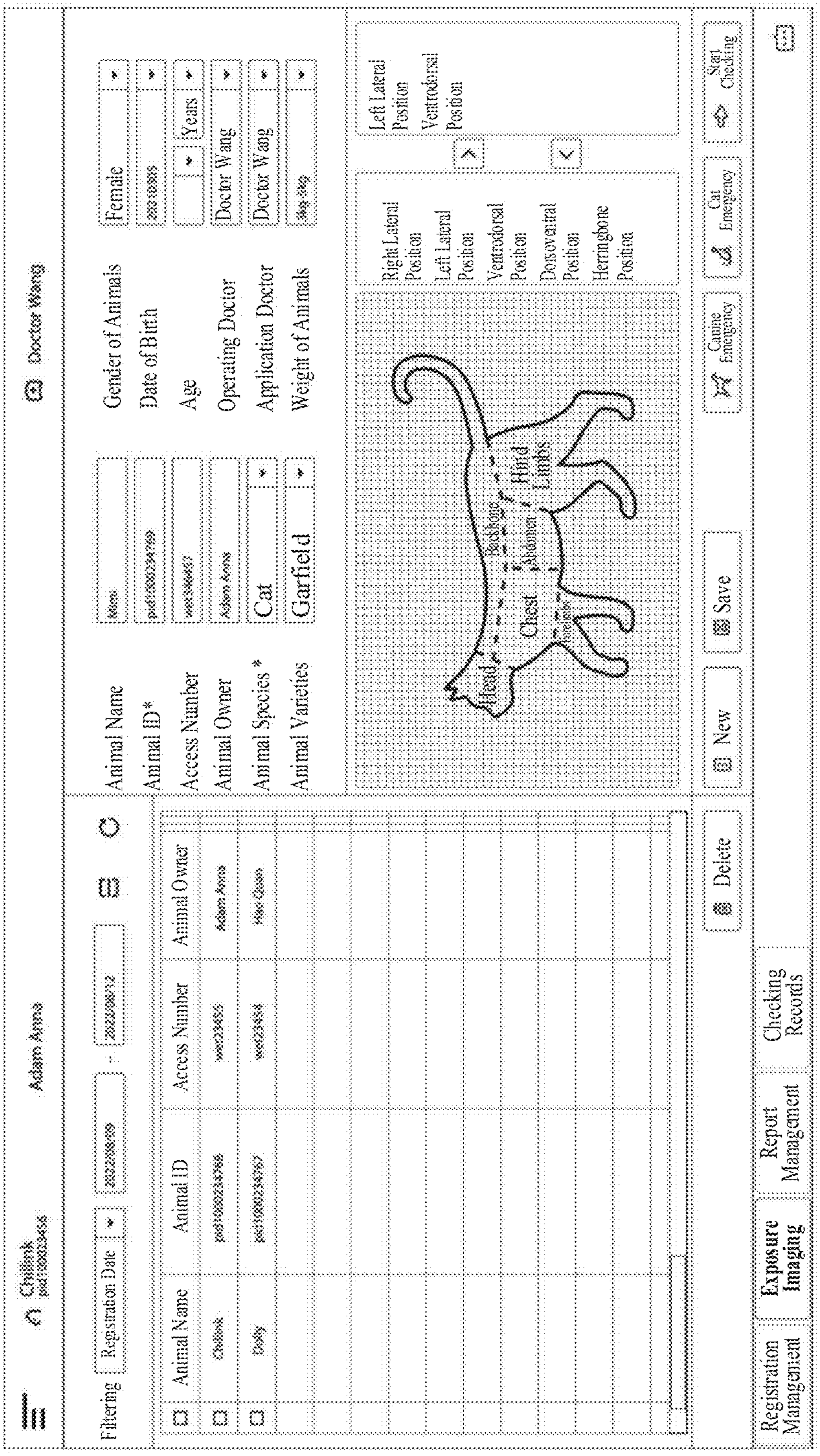
FIG. 3 is a schematic diagram of a selection interface of a veterinary DR device, according to an embodiment.

Exemplarily, FIG. 3 shows a selection interface 300 for a body position to be tested. In the selection interface 300, the user selects two body positions to be tested, namely, a left lateral position and a ventrodorsal position, where the left lateral position is selected first, having a higher priority, the left lateral position is used as a current body position, and when a new current body position needs to be determined, the ventrodorsal position is used as the new body position.

Figure 4A:
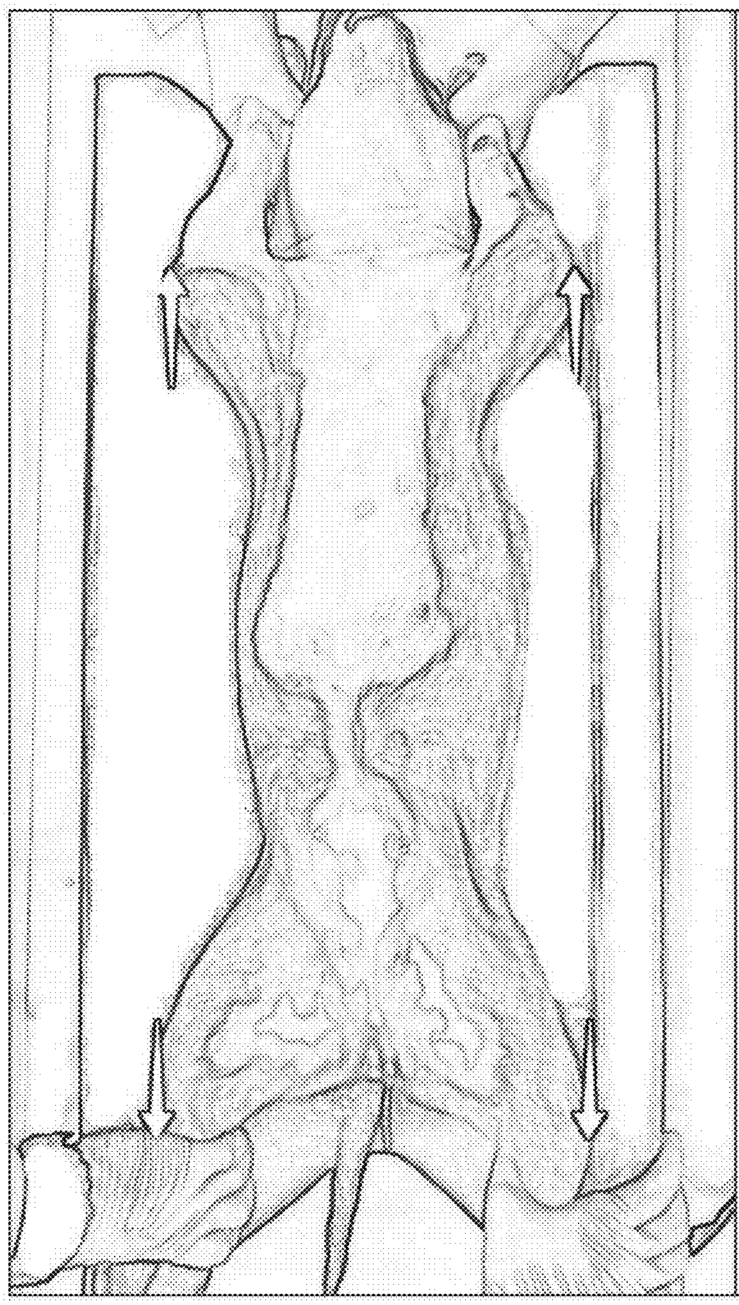
FIG. 4*a* is a schematic diagram of guidance information, according to an embodiment.
Figure 4B:
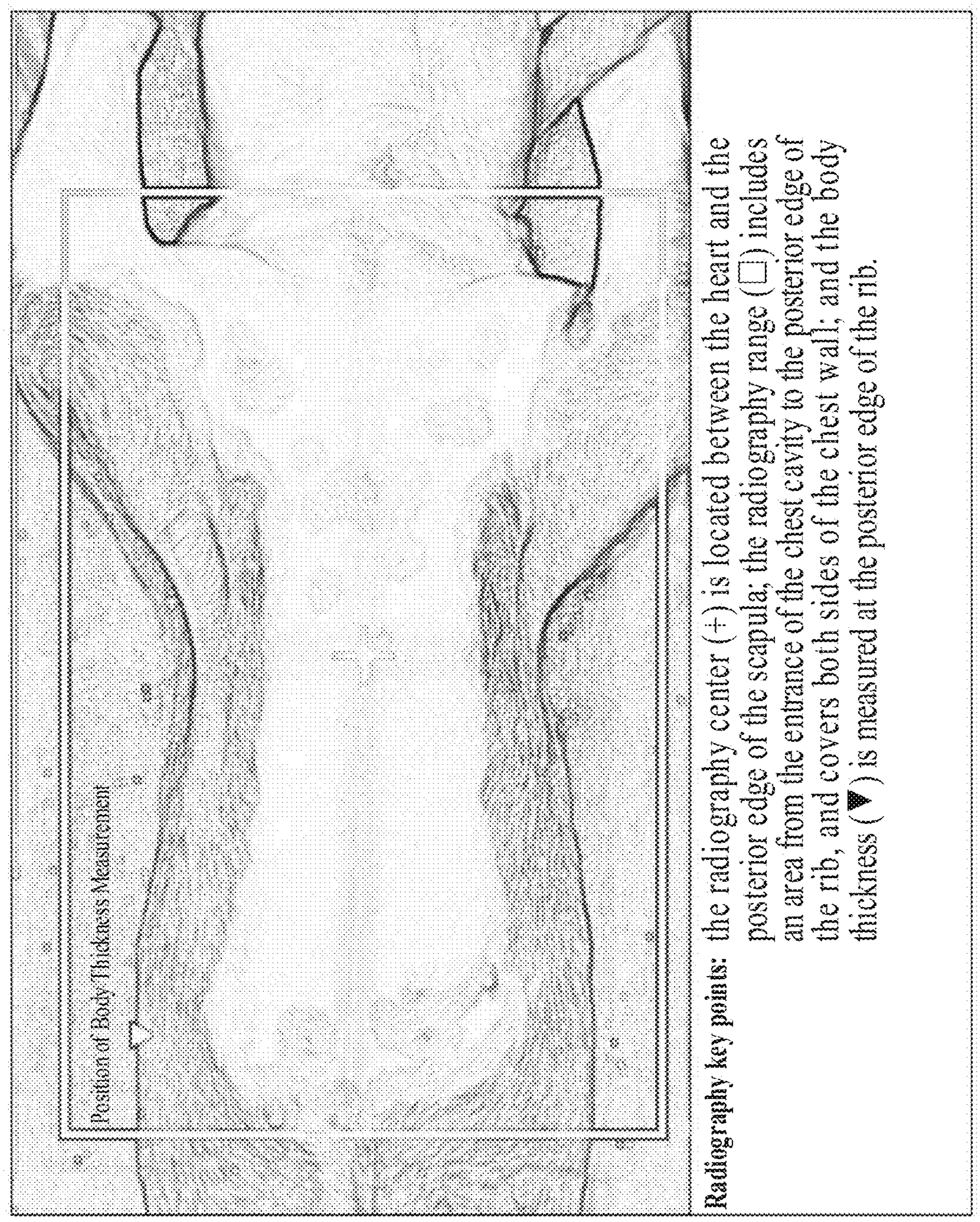
FIG. 4*b* is a schematic diagram of guidance information, according to another embodiment.

In some embodiments, the guidance information includes a plurality of guidance image frames, each of the guidance image frames includes an illustration and/or description of at least one capturing key point used when capturing a medical image. The guidance image frame may be a frame of static images or a frame of dynamic images. When the guidance information for the current body position is displayed, the plurality of guidance image frames for the current body position are played according to an order of the capturing key point. Exemplarily, FIG. 4*a* and FIG. 4*b* are schematic diagrams of a plurality of guidance image frames in one piece of guidance information, including both a positioning illustration for an animal during actual capture of a medical image and operation instructions for the capture. After each guidance image frame is displayed on a display interface 500 for n seconds, a guidance image frame for a next capturing key point is displayed. The above guidance image frame can form a guidance video, and in addition to the guidance image frame, the guidance video may include image frames for other content.

In some embodiments, the user may pause continuous displaying (that is, playing) of the plurality of guidance image frames by an operation. When the user pauses the playing of the plurality of guidance image frames, a currently displayed guidance image frame may stay on the display 60, so that the user may carefully view the currently displayed guidance image frame.

In some embodiments, the plurality of guidance image frames for the current body position are displayed circularly until the user stops displaying the guidance information by an operation. For example, a button to stop playing the guidance information may be provided on the display interface 500, and the user stops playing the plurality of guidance image frames after pressing the button.

In some other embodiments, the displaying of the guidance information for the current body position is stopped based on that the user starts obtaining the medical image. After the processor 50 detects that the user starts obtaining the medical image for the body position to be tested, the veterinary DR device automatically stops displaying the guidance information for the current body position. Considerations of such a design are as follows: the obtaining of the medical image has already been started, the displaying of the guidance information is not helpful to the current capturing or of limited help to the current capturing, and therefore, the displaying of the guidance information is automatically stopped to avoid distracting medical care personnel.

In some embodiments, the user starts exposure through a hand switch of the veterinary DR device and controls to start obtaining medical images. After the processor 50 detects an exposure start instruction input by the user when operating the hand switch, the display 60 is controlled to stop displaying the guidance information for the current body position. An advantage in doing this is that a linkage is established between the exposure operation and the displaying of the guidance information, and the step of stopping the displaying of the guidance information is integrated into a natural operation of the user, thus reducing a learning cost of the user.

After the exposure is started, it usually takes a certain exposure time to obtain the medical image. In other words, starting exposure and completing exposure are two concepts. In some embodiments above, after the exposure is started, the displaying of the guidance information for the current body position may be stopped. However, in some other embodiments, during the period of starting the exposure and waiting for the completion of the exposure, the guidance information for the current body position may also be displayed continuously.

In this embodiment, after the medical image for the current body position is obtained, that is, after the exposure is completed, the veterinary DR device may automatically jump to the guidance for capturing the medical image for the next body position to be tested. Specifically, the processor 50 may detect whether the obtaining of the medical image for the current body position is completed. The next body position to be tested is used as a new current body position, according to a specified order after it is detected that the obtaining of the medical image for the current body position is completed, and the display 60 is controlled to display the guidance information for the new current body position. For example, as explained above, a next-priority body position to be tested is used as the new current body position, and then the guidance information for the body position to be tested is displayed.

It may be seen from the above description that, when medical images for a plurality of body positions to be tested need to be obtained, the veterinary DR device in this embodiment plays corresponding guidance information for obtaining the medical image that is for each body position to be tested. This assists the user in capturing the medical image for the body position to be tested. After obtaining the medical image for the body position to be tested is completed, the veterinary DR device can automatically display, without further operations of the user, the guidance information for the next body position to be tested, so as to assist the user to capture the medical image for the next body position to be tested. Therefore, the user can concentrate on adjusting a posture or body position of the animal 70 to be tested, which is convenient for continuously obtaining the medical images for the plurality of body positions to be tested.

In some embodiments, the user also completes exposure through a hand switch of the veterinary DR device. For example, during the exposure, the user presses the hand switch to stop the exposure, which means that obtaining the medical image is completed. In some embodiments, after the processor 50 detects an exposure completion instruction input by the user when operating the hand switch, timing is started. When a timing duration reaches a preset duration, the next body position to be tested is used as the new current body position, and the guidance information for the new current body position is displayed. In other words, after obtaining the medical image is completed, the veterinary DR device does not immediately update the current body position and display the guidance information for the new current body position, but waits for a period of time, during which the user may complete various operations, including but not limited to: adjusting, according to the next body position to be tested, the posture of the animal 70 to be tested, adjusting the position of each module in the veterinary DR device, and observing the image quality of the obtained medical image, to ensure that the user has sufficient operation time. It may be understood that it is only an exemplary method to determine whether the obtaining of the medical image is completed by detecting an operation of the user on the hand switch, and detecting other operations that can trigger the exposure completion instruction to determine whether the obtaining of the medical image is completed falls within the protection scope of this embodiment.

After the processor 50 starts timing, a countdown before displaying the guidance information for the next body position to be tested may also be obtained based on a relationship between a timing duration and the preset duration, and the display 60 may be controlled to display the countdown. For example, the preset duration is 30 seconds. When the processor 50 detects that the obtaining of the medical image is completed, the display 60 starts displaying the countdown of 30 seconds, and when the countdown reaches 0 seconds, the display 60 starts playing guidance information for the new current body position, that is, the guidance information for the next body position to be tested.

In conclusion, intuitively from the perspective of the user, the displayed guidance information can be helpful when obtaining the medical image for the current body position. The hand switch is operated after preparation for the capturing based on the guidance information, for example, an exposure start button on the hand switch is pressed, and the display 60 stops displaying the guidance information while the exposure start button is pressed. Then, during the exposure, the user operates the hand switch again, for example, presses an exposure completion button on the hand switch, the countdown starts to be displayed on the display 60, and the user may arrange the work at hand according to the duration of the countdown. After the countdown ends, the display 60 starts displaying the guidance information for the new current body position, and the user may continue with the capture of the medical image for the new current body position based on the guidance information. The whole process does not require the user to pay too much learning cost or price, and the user may complete the usage of the veterinary DR device in this embodiment according to existing habits of operating the veterinary DR device.

In some other embodiments, the processor 50 starts timing and monitors whether a user operation is received when the exposure completion instruction is detected. When a timing duration reaches a preset duration and no user operation is received, the next body position to be tested is used as the new current body position, and the guidance information for the new current body position is displayed. The operation herein may be a specific operation, for example, an operation of adjusting an exposure parameter by the user; and the operation herein may alternatively be any operation of the user, for example, the user presses any button on the display 60. In this embodiment, the operation of the user may interrupt a process of displaying the guidance information for the next body position to be tested, and may be applied to the following scenarios. After a medical image is obtained, if the user thinks that the image quality of the medical image does not meet expectations, and prepares to obtain a medical image for the current body position again, the user may prevent, through specific or arbitrary operations, the veterinary DR device from entering the capturing guidance for the next body position to be tested, so as to give the user time to continue to obtain a medical image for the current body position. Based on this embodiment, the processor 50 may also obtain, according to a relationship between the timing duration and the preset duration, a countdown before displaying the guidance information for the next body position to be tested, and the display 60 may be controlled to display the countdown. If a user operation is detected within the preset duration, the countdown is also terminated. For example, the preset duration is 30 seconds. When the processor 50 detects that the obtaining of the medical image is completed, the display 60 starts displaying the countdown of 30 seconds. When there are 10 seconds left in the countdown, the user operates the veterinary DR device, the displayed countdown disappears or stays at 10 seconds, so as to prompt the user to stop jumping to the capturing guidance for the next body position to be tested. During the period of stopping jumping, the user may continue to obtain the medical image for the current body position. In addition, the veterinary DR device may also provide an operation entry for replaying the guidance information for the current body position, and the user may continue to view the guidance information for the current body position through the operation entry, so as to obtain the capturing assistance for the medical image for the current body position again. When the processor 50 detects a selection instruction of the user for another body position to be tested, the selected body position to be tested is used as the new current body position, and the display 60 is controlled to display the guidance information for the new current body position. In other words, after the user obtains the medical image, the veterinary DR device may automatically jump to the capturing guidance for the next body position to be tested, and a user operation may stop the jumping during the preparation for the jumping. After the jumping is stopped, the user may continue to call the guidance information for the current body position to obtain capturing assistance, and then the user may select any body position to be tested as the new current body position, so that the veterinary DR device may continue to jump to the capturing guidance for the new current body position.

Figure 5A:
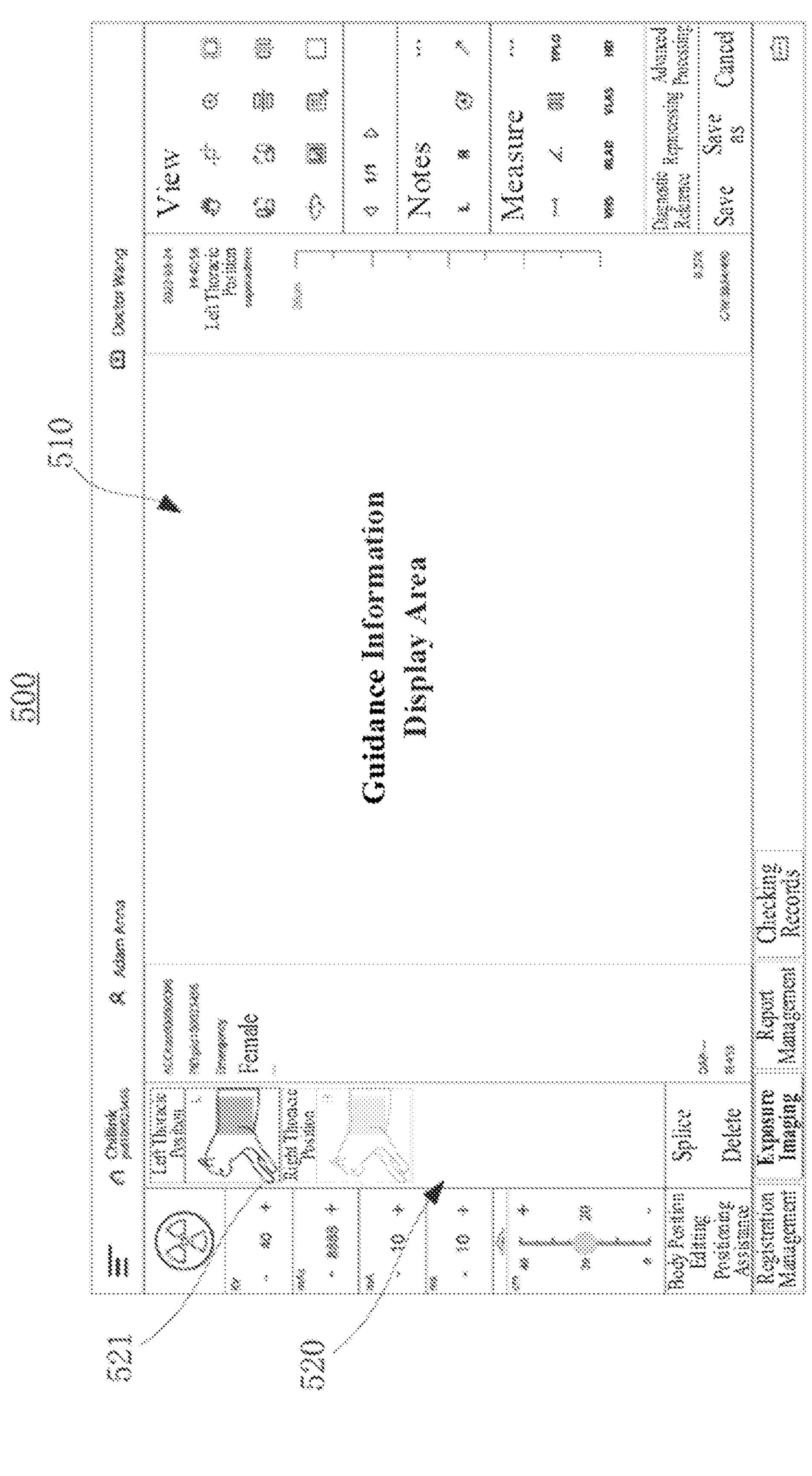
FIG. 5*a* is a schematic diagram of a display interface of a veterinary DR device, according to an embodiment.
Figure 5B:
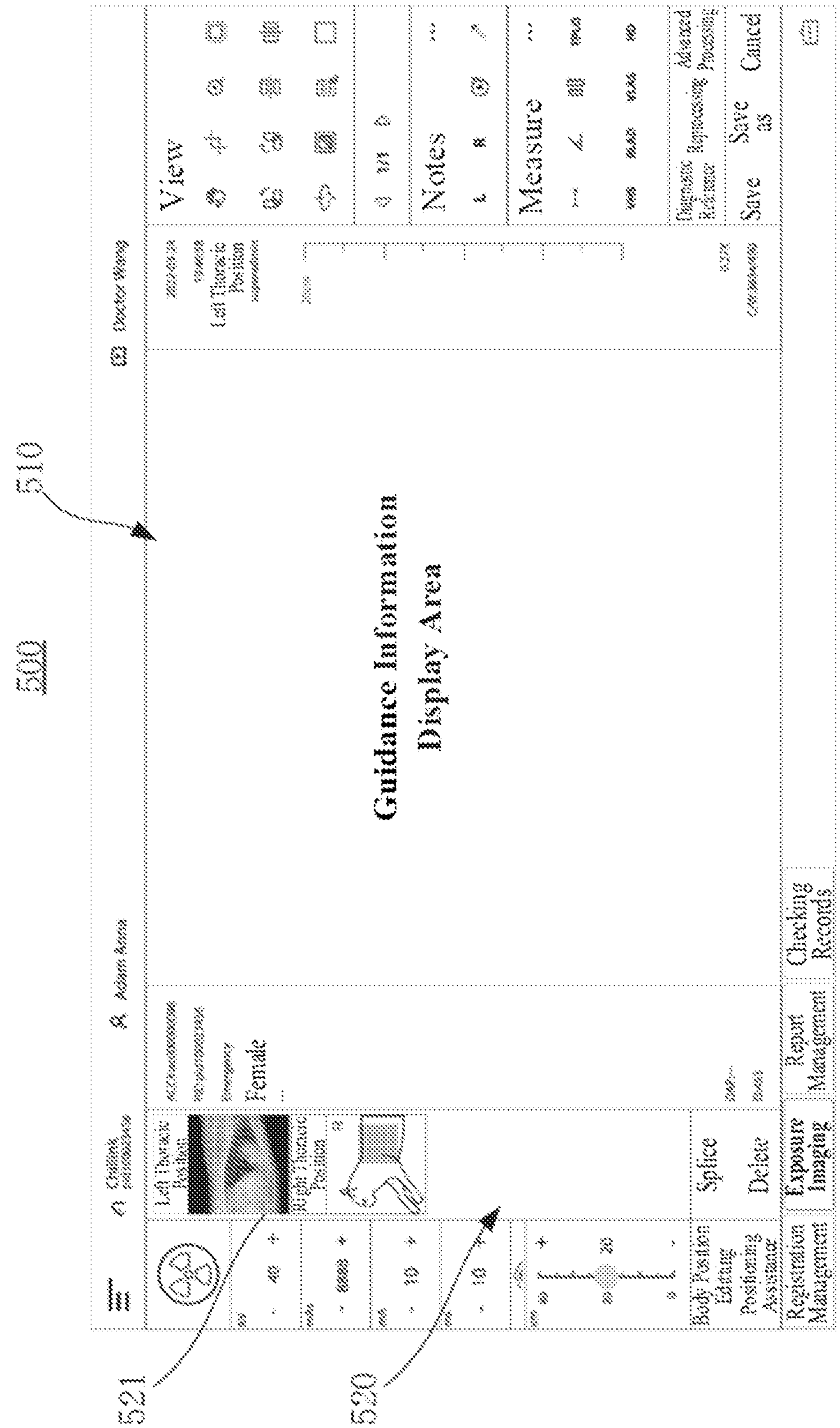
FIG. 5*b* is a schematic diagram of a display interface of a veterinary DR device, according to another embodiment.
Figure 5C:
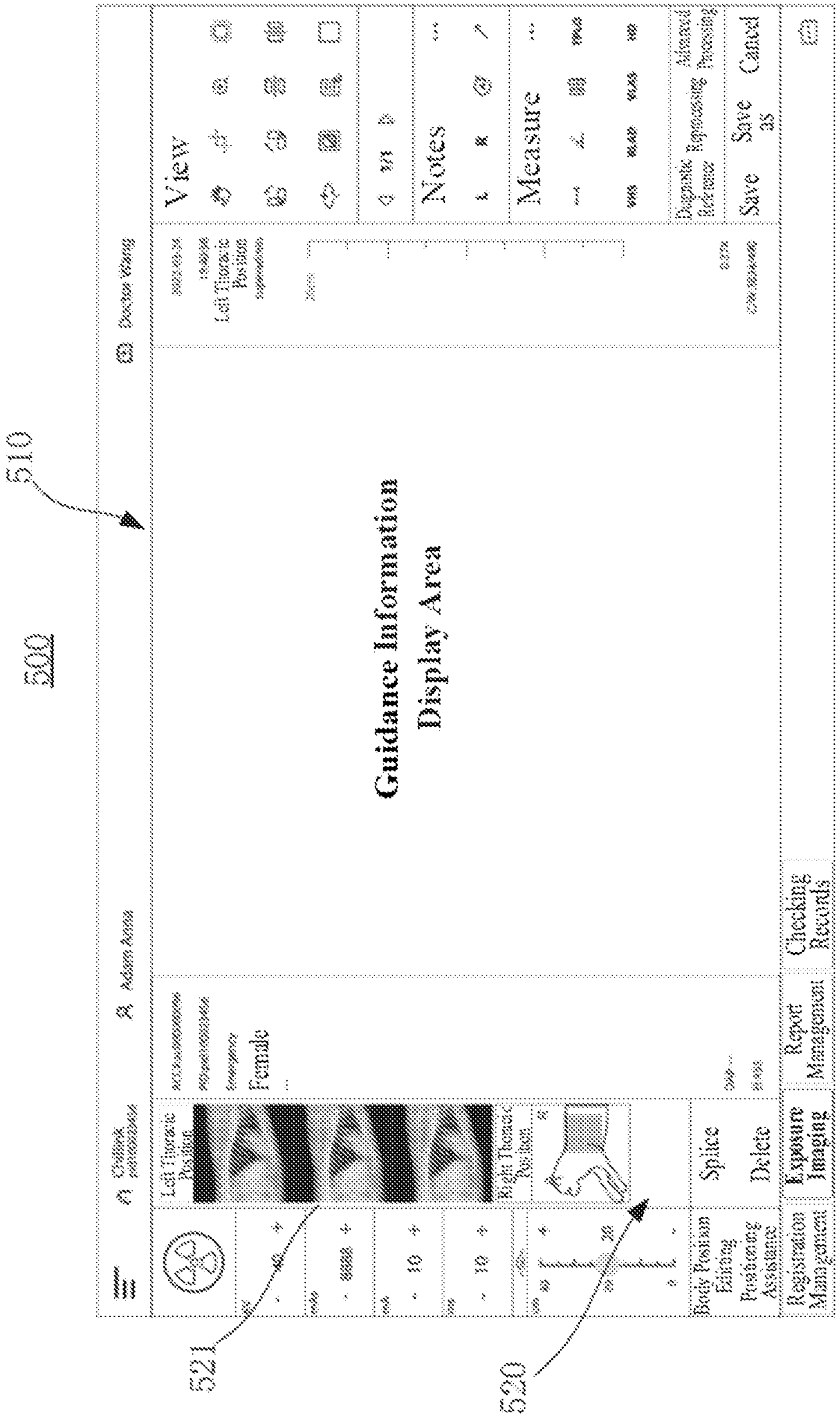
FIG. 5*c* is a schematic diagram of a display interface of a veterinary DR device, according to still another embodiment.

In some embodiments, the display interface 500 provided by the display 60 is shown in FIG. 5*a* to FIG. 5*c*. The display interface 500 includes a first display area 510 and a second display area 520, where the first display area 510 is used for displaying guidance information and the second display area 520 includes thumbnail areas 521 respectively corresponding to at least two body positions to be tested. As shown in FIG. 5*a*, when a medical image for a body position to be tested has not been obtained, a positioning schematic diagram of the body position to be tested is displayed in the thumbnail area 521 corresponding to the body position to be tested, and the user may have, through the positioning schematic diagram, an intuitive understanding of the body position to be tested. After the medical image corresponding to the body position to be tested is obtained, the processor 50 resizes the medical image based on a size of the thumbnail area 521, such that a size of the medical image is the same as that of the thumbnail area 521. Then, as shown in FIG. 5*b*, the medical image is overlaid on the positioning schematic diagram, and intuitively, the medical image is pasted in the thumbnail area 521.

When at least two medical images for a body position to be tested are obtained, a latest obtained medical image is pasted in the thumbnail area 521, that is, every time a latest medical image is obtained, content displayed in the thumbnail area 521 is replaced with the latest medical image, and other medical images are displayed in the second display area 520 in a preset arrangement order. For example, in FIG. 5*c*, medical images corresponding to [a left thoracic position] are sequentially arranged vertically in a manner of extending downwards, and the user may clearly know which medical image was obtained at which time through a plurality of medical images arranged in order, so as to avoid confusion when obtaining a plurality of medical images for a body position to be tested.

Figure 6:
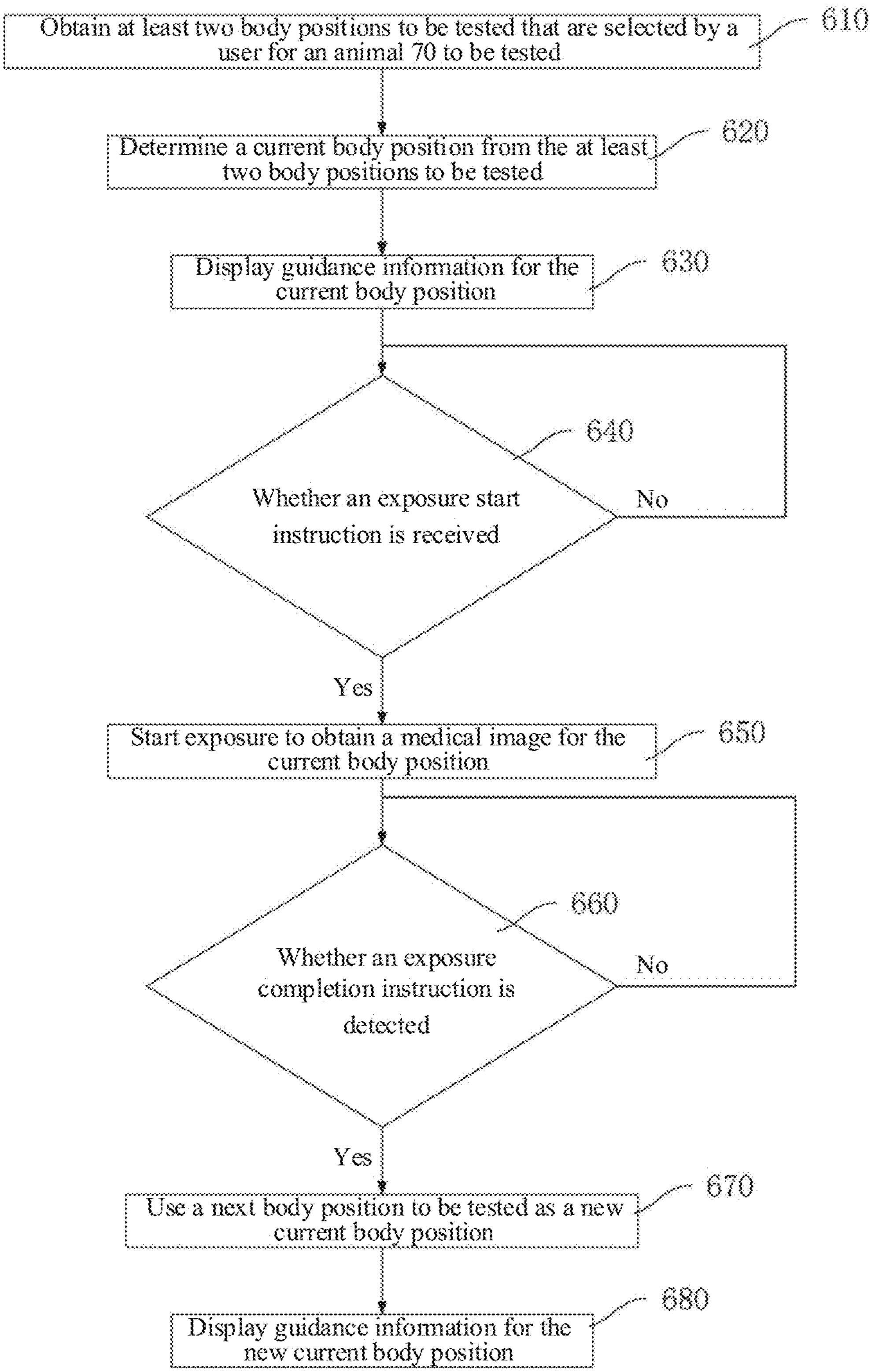
FIG. 6 is a flowchart of a capturing guidance method for a veterinary DR device, according to an embodiment.

FIG. 6 shows a capturing guidance method for a veterinary DR device, including the following steps.

In step 610, at least two body positions to be tested that are selected by a user for an animal 70 to be tested are obtained.

Each of the body positions to be tested has a piece of preset guidance information, and each piece of guidance information is used for assisting the user to capture a medical image for a body position to be tested. Forms of the guidance information include but are not limited to text, pictures, and videos. Content of the guidance information includes but is not limited to a positioning mode of the animal 70 to be tested, an operation key point of the veterinary DR device, etc., to guide the user to obtain a better medical image.

In step 620, a current body position is determined from the at least two body positions to be tested.

In some embodiments, when the user selects the at least two body positions to be tested, corresponding priorities are assigned to the body positions to be tested. For example, when the user selects the at least two body positions to be tested, a body position to be tested that is first selected has a higher priority. Exemplarily, FIG. 3 shows a selection interface 300 for a body position to be tested. In the selection interface 300, the user selects two body positions to be tested, namely, a left lateral position and a ventrodorsal position, where the left lateral position is selected first, having a higher priority, the left lateral position is used as a current body position, and when a new current body position needs to be determined, the ventrodorsal position is used as the new body position.

In step 630, guidance information for the current body position is displayed.

In some embodiments, the guidance information includes a plurality of guidance image frames, each of the guidance image frames includes an illustration and/or description of at least one capturing key point used when capturing a medical image. The guidance image frame may be a frame of static images or a frame of dynamic images. When the guidance information for the current body position is displayed, the plurality of guidance image frames for the current body position are played according to an order of the capturing key point. Exemplarily, FIG. 4*a* and FIG. 4*b* are schematic diagrams of a plurality of guidance image frames in one piece of guidance information, including both a positioning illustration for an animal during actual capture of a medical image and operation instructions for the capture. After each guidance image frame is displayed on a display interface 500 for n seconds, a guidance image frame for a next capturing key point is displayed. The above guidance image frame can form a guidance video, and in addition to the guidance image frame, the guidance video may include image frames for other content.

In some embodiments, the user may pause continuous displaying (that is, play) of the plurality of guidance image frames by an operation. When the user pauses playing of the plurality of guidance image frames, a currently displayed guidance image frame may stay on the display interface 500, so that the user may carefully view the currently displayed guidance image frame.

In some embodiments, the plurality of guidance image frames for the current body position are displayed circularly until the user stops displaying the guidance information by an operation. For example, a button for stopping playing the guidance information may be provided on the display interface 500, and the user stops playing the plurality of guidance image frames after pressing the button.

In some embodiments, the display interface 500 is shown in FIG. 5*a* to FIG. 5*c*. The display interface 500 includes a first display area 510 and a second display area 520, wherein the first display area 510 is used for displaying guidance information and the second display area 520 includes thumbnail areas 521 respectively corresponding to at least two body positions to be tested. As shown in FIG. 5*a*, when a medical image for a body position to be tested has not been obtained, a positioning schematic diagram of the body position to be tested is displayed in the thumbnail area 521 corresponding to the body position to be tested, and the user may have, through the positioning schematic diagram, an intuitive understanding of the body position to be tested. After the medical image corresponding to the body position to be tested is obtained, the medical image is resized based on a size of the thumbnail area 521, such that a size of the medical image is the same as that of the thumbnail area 521. Then, as shown in FIG. 5*b*, the medical image is overlaid on the positioning schematic diagram, and intuitively, the medical image is pasted in the thumbnail area 521.

When at least two medical images for a body position to be tested are obtained, a latest obtained medical image is pasted in the thumbnail area 521, that is, every time a latest medical image is obtained, content displayed in the thumbnail area 521 is replaced with the latest medical image, and other medical images are displayed in the second display area 520 in a preset arrangement order. For example, in FIG.

5*c*, medical images corresponding to [a left thoracic position] are sequentially arranged vertically in a manner of extending downwards. The user may clearly know which medical image was obtained at which time through a plurality of medical images arranged in order, so as to avoid confusion when obtaining a plurality of medical images for a body position to be tested.

In step 640, whether an exposure start instruction input by the user is received is determined, where if an exposure start instruction is received, step 650 is performed, otherwise, step 640 continues to be performed.

In some embodiments, after the exposure start instruction is received, the displaying of the guidance information for the current body position is automatically stopped. Considerations of such a design are as follows: the obtaining of the medical image has already been started, the displaying of the guidance information is not helpful to the current capturing or of limited help to the current capturing, and therefore, the displaying of the guidance information is automatically stopped to avoid distracting medical care personnel.

In some embodiments, the user inputs the exposure start instruction by operating a hand switch of the veterinary DR device, intuitively, after the user operates the hand switch, the veterinary DR device may automatically stop displaying the guidance information for the current body position. An advantage in doing this is that a linkage is established between the exposure operation and the displaying of the guidance information, and the step of stopping displaying the guidance information is integrated into a natural operation of the user, thus reducing a learning cost of the user.

In step 650, exposure is started to obtain a medical image for the current body position.

After the exposure is started, it usually takes a certain exposure time to obtain the medical image. In other words, starting exposure and completing exposure are two concepts. In some embodiments above, after the exposure is started, the displaying of the guidance information for the current body position may be stopped. However, in some other embodiments, during the period of starting the exposure and waiting for the completion of the exposure, the guidance information for the current body position may also be displayed continuously.

In step 660, whether an exposure completion instruction is triggered based on completion of obtaining the medical image for the current body position is detected is determined. If an exposure completion instruction is detected, step 670 is performed, otherwise, step 660 continues to be performed.

In some embodiments, the user also completes exposure through a hand switch of the veterinary DR device. For example, during the exposure, the user presses the hand switch to trigger the exposure completion instruction, which means that obtaining the medical image is completed. It may be understood that it is only an exemplary method to determine whether the obtaining of the medical image is completed by detecting an operation of the user on the hand switch, and detecting other operations that can trigger the exposure completion instruction to determine whether the obtaining of the medical image is completed falls within the protection scope of this embodiment.

In step 670, a next body position to be tested is used as a new current body position according to a specified order. For example, as explained above, a next-priority body position to be tested is used as the new current body position. In other embodiments, the specified order may alternatively be a system default order, for example, some body positions to be tested are preset to be prioritized as the current body position, which is independent of the selection order of the user.

In step 680, guidance information for the new current body position is displayed.

It may be seen from the above description that, when medical images for a plurality of body positions to be tested need to be obtained, the veterinary DR device in this embodiment plays corresponding guidance information for obtaining the medical image that is for each body position to be tested, so as to assist the user to capture the medical image for the body position to be tested. After obtaining of the medical image for the body position to be tested is completed, the veterinary DR device can automatically display, without other operations of the user, the guidance information for the next body position to be tested, so as to assist the user to capture the medical image for the next body position to be tested. Therefore, the user can concentrate on adjusting a posture or body position of the animal 70 to be tested, which is convenient for continuously obtaining the medical images for the plurality of body positions to be tested.

In some embodiments, timing is started when the exposure completion instruction is detected, and steps 670 and 680 are performed only when a timing duration reaches a preset duration. In other words, after the obtaining of the medical image is completed, the veterinary DR device does not immediately update the current body position and display the guidance information for the new current body position, but waits for a period of time, during which the user may complete various operations, including but not limited to: adjusting, according to the next body position to be tested, the posture of the animal 70 to be tested, adjusting the position of each module in the veterinary DR device, and observing the image quality of the obtained medical image, so that the user have sufficient operation time. In some other embodiments, after the timing is started, a countdown before displaying the guidance information for the next body position to be tested may also be obtained based on a relationship between the timing duration and the preset duration, and the countdown is displayed on the display interface 500. For example, the preset duration is 30 seconds. When it is detected that the obtaining of the medical image is completed, the display interface 500 starts displaying the countdown of 30 seconds, and when the countdown reaches 0 seconds, the guidance information for the new current body position, that is, the guidance information for the next body position to be tested starts to be played.

In some embodiments, the timing is started and whether a user operation is received is monitored when the exposure completion instruction is detected, and steps 670 and 680 are performed only when a timing duration reaches a preset duration and no user operation is received. The operation herein may be a specific operation, for example, an operation of adjusting an exposure parameter by the user. The operation herein may alternatively be any operation of the user. In other words, the operation of the user may interrupt a process of displaying the guidance information for the next body position to be tested, and may be applied to the following scenarios. After a medical image is obtained, if the user thinks that the image quality of the medical image does not meet expectations, and prepares to obtain a medical image for the current body position again, the user may prevent, through specific or arbitrary operations, the veterinary DR device from entering the capturing guidance for the next body position to be tested, so as to give the user time to continue to obtain a medical image for the current body position. Based on this embodiment, a countdown before displaying the guidance information for the next body position to be tested may also be obtained based on a relationship between the timing duration and the preset duration, and the countdown is displayed on the display interface 500. If a user operation is detected within the preset duration, the countdown is also terminated. For example, the preset duration is 30 seconds. When it is detected that the obtaining of the medical image is completed, the display interface 500 starts displaying the countdown of 30 seconds; and when there are 10 seconds left in the countdown, the user operates the veterinary DR device, the displayed countdown disappears or stays at 10 seconds, so as to prompt the user to stop jumping to the capturing guidance for the next body position to be tested, and during the period of stopping jumping, the user may continue to obtain the medical image for the current body position. In addition, the veterinary DR device may also provide an operation entry for replaying the guidance information for the current body position, and the user may continue to view the guidance information for the current body position through the operation entry, so as to obtain the capturing assistance for the medical image for the current body position again. When a selection instruction of the user for another body position to be tested is detected, the selected body position to be tested is used as the new current body position, and the guidance information for the new current body position is displayed. In other words, after the user obtains the medical image, the veterinary DR device may automatically jump to the capturing guidance for the next body position to be tested, and a user operation may stop the jumping during the preparation for the jumping. After the jumping is stopped, the user may continue to call the guidance information for the current body position to obtain capturing assistance, and then the user may select any body position to be tested as the new current body position, so that the veterinary DR device may continue to jump to the capturing guidance for the new current body position.

According to the veterinary DR device and the capturing guidance method therefor in the above embodiments, the guidance information for the current body position is provided when the medical image for the current body position is obtained. When the obtaining of the medical image for the current body position is completed, the device may automatically jump to the capturing guidance for the next body position to be tested, which is convenient for the user to continuously capture medical images of the animal to be tested in a plurality of body positions to be tested. In addition, an operation of a user is almost the same as that of the existing veterinary DR device, which integrates displaying the guidance information and stopping displaying the guidance information into the normal operation of the user, and reduces the learning cost of the user.

Descriptions are provided herein with reference to various exemplary embodiments. However, those skilled in the art should understand that changes and corrections may be made to the exemplary embodiments without departing from the scope of this specification. For example, various operational steps and assemblies for executing the operational steps may be implemented in different methods on the basis of specific applications or in consideration of any number of cost functions associated with operations of the system (for example, one or more steps may be deleted, modified or incorporated into other steps).

In addition, those skilled in the art can understand that the principles herein may be reflected in a computer program product in a computer-readable storage medium, where the readable storage medium is loaded with computer-readable program codes in advance. Any tangible non-transitory computer-readable storage medium may be used, including a magnetic storage device (a hard disk, a floppy disk, or the like), an optical storage device (CD-ROM, DVD, Blu-ray disc, or the like), a flash memory, and/or the like. These computer program instructions may be loaded on a general-purpose computer, a special-purpose computer, or other programmable data processing devices to form a machine, such that these instructions, when executed on a computer or other programmable data processing apparatuses, may produce a means for implementing a specified function. These computer program instructions may alternatively be stored in a computer-readable memory. The computer-readable memory may instruct a computer or other programmable data processing devices to operate in a particular manner, such that the instructions stored in the computer-readable memory may produce an article of manufacture which includes a means for implementing a specified function. The computer program instructions may alternatively be loaded onto a computer or other programmable data processing devices to perform a series of operational steps on the computer or other programmable devices to produce a computer-implemented process, such that the instructions, when executed on the computer or other programmable devices, may provide steps for implementing a specified function.

Although the principles herein are shown in various embodiments, many modifications of structures, arrangements, proportions, elements, materials, and components particularly applicable to specific environmental and operating requirements may be made without departing from the principles and scope of the disclosure. These modifications and other changes or corrections fall within the scope of this specification.

The foregoing detailed descriptions are provided with reference to various embodiments. However, those skilled in the art should understand that various corrections and changes may be made without departing from the scope of the disclosure. Therefore, the disclosure is intended for an illustrative purpose other than a limitative purpose, and all of these modifications fall within the scope of the disclosure. Similarly, the advantages, other advantages, and solutions to problems of the various embodiments are described above. However, the benefits, the advantages, the solutions to the problems, and any of their contributing factors, or solutions clarifying them should not be construed to be critical, necessary, or essential. The term “include” used herein and any other variations thereof all refer to a non-exclusive inclusion, such that a process, method, article, or device, including a list of elements includes not only these elements, but also other elements that are not expressly listed or not inherent to the process, method, system, article, or device. In addition, the term “couple” used herein and any other variations thereof refer to a physical connection, an electrical connection, a magnetic connection, an optical connection, a communication connection, a functional connection, and/or any other connections.

Those skilled in the art should understand that many changes may be made to the details of the foregoing embodiments without departing from the basic principles of the disclosure. Therefore, the scope of the disclosure should be determined in accordance with the following claims.

What is claimed is:

1. A veterinary digital X-ray photography system, comprising:

a display;

an X-ray emission module configured to generate an X-ray to penetrate an animal to be tested;

an X-ray receiving module configured to receive the X-ray generated by the X-ray emission module, to convert received the X-ray into electric signals;

an imaging module configured to obtain a medical image based on the electric signals converted by the X-ray receiving module;

a memory configured to store a plurality of pieces of guidance information, wherein each piece of guidance information is used for assisting a user to capture a medical image of the animal to be tested in a body position to be tested and comprises a plurality of guidance image frames, with each of the guidance image frames comprising an illustration and/or description of at least one capturing key point to be used when capturing a medical image; and a processor configured to obtain at least two body positions to be tested that are selected by the user for the animal to be tested, determine a current body position from the at least two body positions to be tested, and control the display to display guidance information for the current body position;

wherein, after receiving an exposure start instruction input by the user, the processor is further configured to: (a) control the X-ray emission module to emit the X-ray to the animal to be tested for the purpose of obtaining a medical image for the body position, (b) control the imaging module to obtain the medical image for the current body position based on the electric signal converted by the X-ray receiving module, and (c) after detecting an exposure completion instruction triggered based on completion of obtaining the medical image for the current body position, prompt a next body position to be tested as a new current body position according to a specified order and control the display to automatically display guidance information for the new current body position without an instruction from the user.

2. The digital X-ray photography system of claim 1, wherein after detecting an exposure completion instruction triggered based on completion of obtaining the medical image for the current body position, the prompting a next body position to be tested as a new current body position according to a specified order comprises:

starting timing when the exposure completion instruction is detected, and when a timing duration reaches a preset duration, using the next body position to be tested as the new current body position according to the specified order.

3. The digital X-ray photography system of claim 1, wherein after detecting an exposure completion instruction triggered based on completion of obtaining the medical image for the current body position, the prompting a next body position to be tested as a new current body position according to a specified order comprises:

starting timing and monitoring whether the user operation is received when the exposure completion instruction is detected, and when a timing duration reaches a preset duration and no user operation is received, using the next body position to be tested as the new current body position according to the specified order.

4. The digital X-ray photography system of claim 1, wherein in a process of displaying, by the display, the guidance information for the current body position, the processor is further configured to:

control, after detecting a display stop instruction input by the user, the display to stop displaying the guidance information for the current body position;

or control, after receiving an exposure start instruction input by the user, the display to stop displaying the guidance information for the current body position.

5. The digital X-ray photography system of claim 4, wherein a display interface of the display comprises thumbnail areas respectively corresponding to the at least two body positions to be tested, wherein before obtaining a medical image for one body position to be tested, the thumbnail area corresponding to the body position to be tested is used for displaying a positioning schematic diagram representing the body position to be tested; and the processor is further configured to:

every time a latest medical image for the current body position is obtained, adjust a size of the latest medical image to adapt to a size of a thumbnail area corresponding to the current body position, and control the display to display the resized latest medical image in the thumbnail area, such that the latest medical image is overlaid on a positioning schematic diagram of the current body position.

6. The digital X-ray photography system of claim 5, wherein after obtaining at least two resized medical images for the current body position, the processor is further configured to:

control, when the display is controlled to display the latest medical image in the thumbnail area, the display to display all obtained resized medical images in a preset arrangement mode.

7. The digital X-ray photography system of claim 1, wherein the controlling the display to display guidance information for the current body position comprises:

controlling the display to display the plurality of guidance image frames for the current body position according to an order of the capturing key point.

8. A method for capturing images in a veterinary digital X-ray photography system, the method comprising:

obtaining at least two body positions to be tested that are selected by a user for an animal to be tested, wherein each of the body positions to be tested has a piece of preset guidance information, and each piece of guidance information is used for assisting the user to capture a medical image for a body position to be tested and comprises a plurality of guidance image frames, with each of the guidance image frames comprising an illustration and/or description of at least one capturing key point to be used when capturing a medical image;

determining a current body position from the at least two body positions to be tested;

displaying guidance information for the current body position;

obtaining a medical image for the current body position after receiving an exposure start instruction input by the user; and after detecting an exposure completion instruction triggered based on completion of obtaining the medical image for the current body position, prompting a next body position to be tested as a new current body position according to a specified order, and automatically displaying guidance information for the new current body position without an instruction from the user.

9. The method of claim 8, wherein after detecting an exposure completion instruction triggered based on completion of obtaining the medical image for the current body position, the prompting a next body position to be tested as a new current body position according to a specified order comprises:

starting timing when the exposure completion instruction is detected, and when a timing duration reaches a preset duration, using the next body position to be tested as the new current body position according to the specified order.

10. The method of claim 8, wherein after detecting an exposure completion instruction triggered based on completion of obtaining the medical image for the current body position, the prompting a next body position to be tested as a new current body position according to a specified order comprises:

starting timing and monitoring whether the user operation is received when the exposure completion instruction is detected, and when a timing duration reaches a preset duration and no user operation is received, using the next body position to be tested as the new current body position according to the specified order.

11. The method of claim 8, wherein the step of displaying guidance information for the current body position further comprises:

stopping displaying the guidance information for the current body position after detecting a display stop instruction input by the user;

or stopping displaying the guidance information for the current body position after receiving an exposure start instruction input by the user.

12. The method of claim 10, further comprising:

providing a display interface, wherein the display interface comprises thumbnail areas respectively corresponding to the at least two body positions to be tested, and before obtaining a medical image for one body position to be tested, the thumbnail area corresponding to the body position to be tested is used for displaying a positioning schematic diagram representing the body position to be tested; and every time a latest medical image for the current body position is obtained, adjusting a size of the latest medical image to adapt to a size of a thumbnail area corresponding to the current body position, and displaying the resized latest medical image in the thumbnail area, such that the latest medical image is overlaid on a positioning schematic diagram of the current body position.

13. The method of claim 12, wherein after obtaining at least two resized medical images for the current body position, the method further comprises:

displaying all obtained resized medical images in a preset arrangement mode when displaying the latest medical image in the thumbnail area.

14. The method of claim 8, wherein the displaying guidance information for the current body position comprises: displaying the plurality of guidance image frames for the current body position according to an order of the capturing key point.

* * * * *